US007037256B2

(12) United States Patent
Osbon et al.

(10) Patent No.: US 7,037,256 B2
(45) Date of Patent: May 2, 2006

(54) METHOD, SYSTEM AND KIT FOR TREATMENT OF PEYRONIE'S DISEASE

(75) Inventors: Julian Osbon, Augusta, GA (US); John Magee, North Augusta, SC (US)

(73) Assignee: Soma Blue, Inc., Augusta, GA (US)

( * ) Notice: Subject to any disclaimer, the term of this patent is extended or adjusted under 35 U.S.C. 154(b) by 700 days.

(21) Appl. No.: 10/271,821

(22) Filed: Oct. 16, 2002

(65) Prior Publication Data

US 2004/0077970 A1 Apr. 22, 2004

(51) Int. Cl.
*A61F 5/00* (2006.01)
(52) U.S. Cl. ...................................... 600/38
(58) Field of Classification Search ............ 600/38–41; 601/6–14
See application file for complete search history.

(56) References Cited

U.S. PATENT DOCUMENTS

| 4,856,498 | A | | 8/1989 | Osbon |
| 5,094,230 | A | * | 3/1992 | Clark, Jr. ...................... 600/38 |
| 5,306,227 | A | | 4/1994 | Osbon et al. |
| 5,624,378 | A | | 4/1997 | Baldecchi |
| 6,183,414 | B1 | * | 2/2001 | Wysor et al. ................. 600/38 |
| 6,306,080 | B1 | | 10/2001 | Mitchell et al. |

OTHER PUBLICATIONS

J. Paul Yurkanin, Effect of Incision and Saphenous Vein Grafting for Peyronie's Disease on Penile Length and Sexual Satisfaction, The Journal of Urology, vol. 166, 1769-1773 (Nov. 2001).

Lawrence S. Hakim, Vacuum Erection Associated Impotence and Peyronie's Disease, The Journal of Urology, vol. 155, 534-535 (Feb. 1996).

Tom F. Lue, Lengthening Shortened Penis Caused by Peyronie's Disease Using Circular Venous Grafting and Daily Stretching With a Vacuum Erection Device, The Journal of Urology, vol. 161, 1141-1144 (Apr. 1999).

* cited by examiner

*Primary Examiner*—John P. Lacyk
(74) *Attorney, Agent, or Firm*—Bracewell & Giuliani LLP

(57) ABSTRACT

A kit and system for treating plaque formation in a patient's extremity are provided. A pressure pump and at least two elongated vacuum chambers are included in the kit and system. Each chamber has a proximal longitudinal end adapted to receive a patient's extremity and a distal longitudinal end adapted to be positioned in fluid communication with the pressure pump so that a pressure is created inside each of the at least two vacuum chambers and exerted upon the extremity received therein when the pressure pump is operating. One of the at least two vacuum chambers has a different inner circumference than another one of the at least two vacuum chambers so that a different level of prevention from bending is provided to the extremity in the direction of the plaque formation with each of the at least two vacuum chambers during operation of the pressure pump. Methods for treating plaque formation in a patient's extremity are also provided.

26 Claims, 10 Drawing Sheets

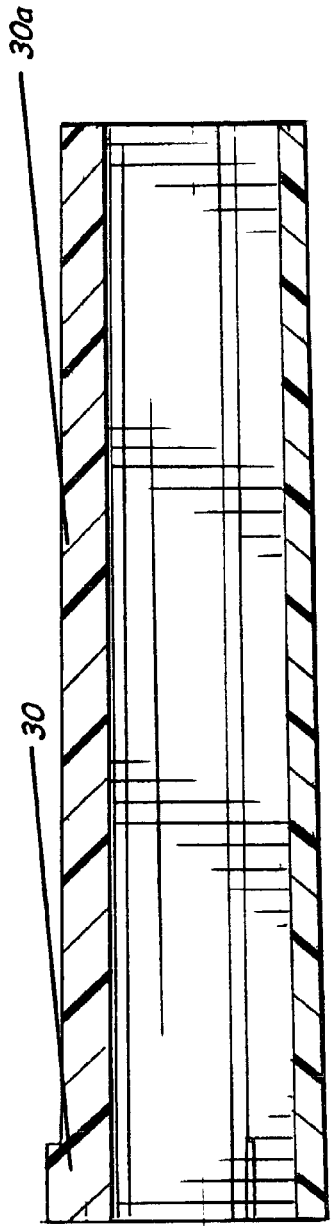
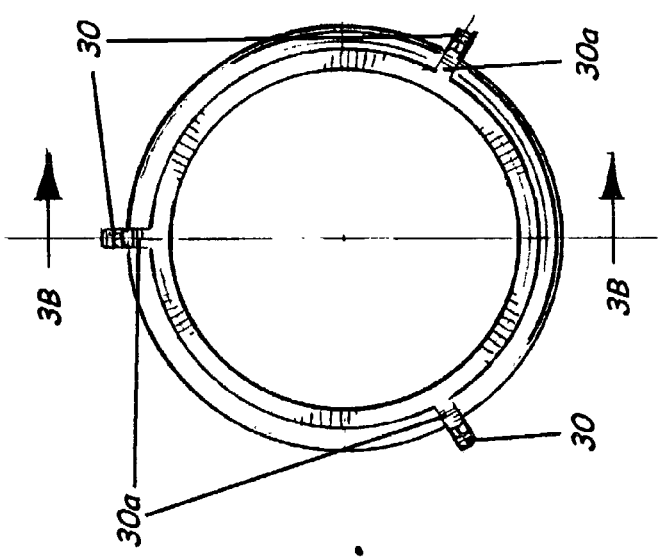
FIG. 3B.
FIG. 3A.

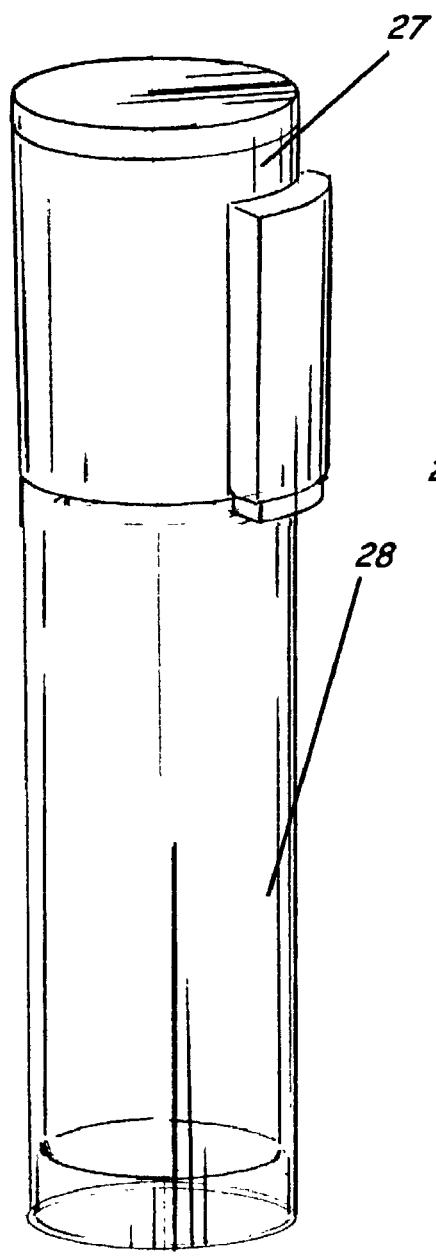
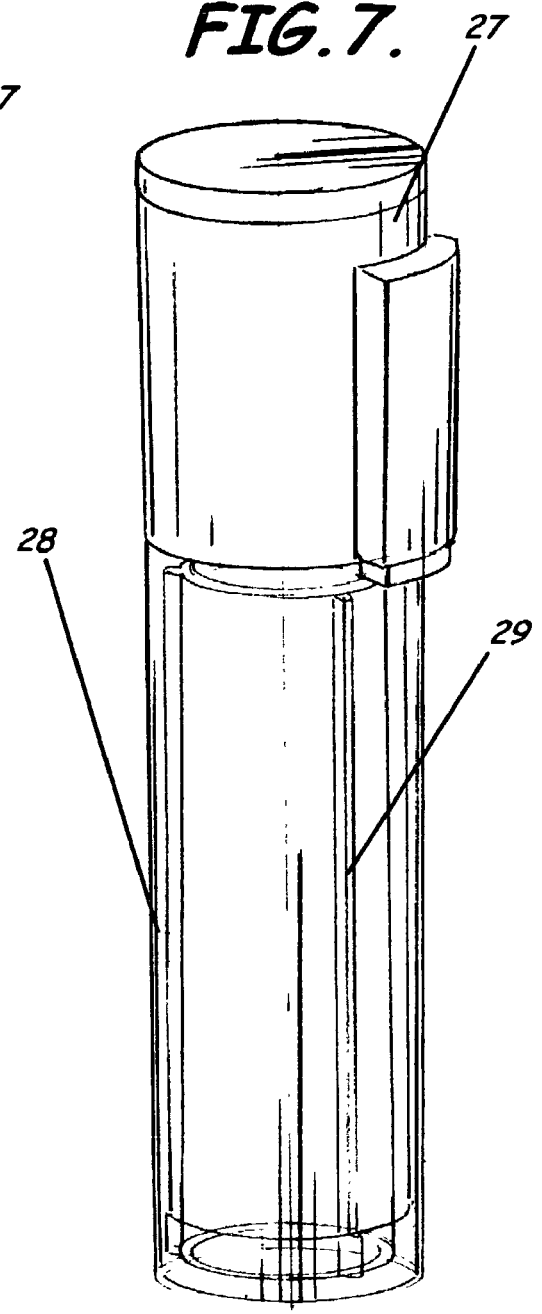

FIG.8.
FIG.9
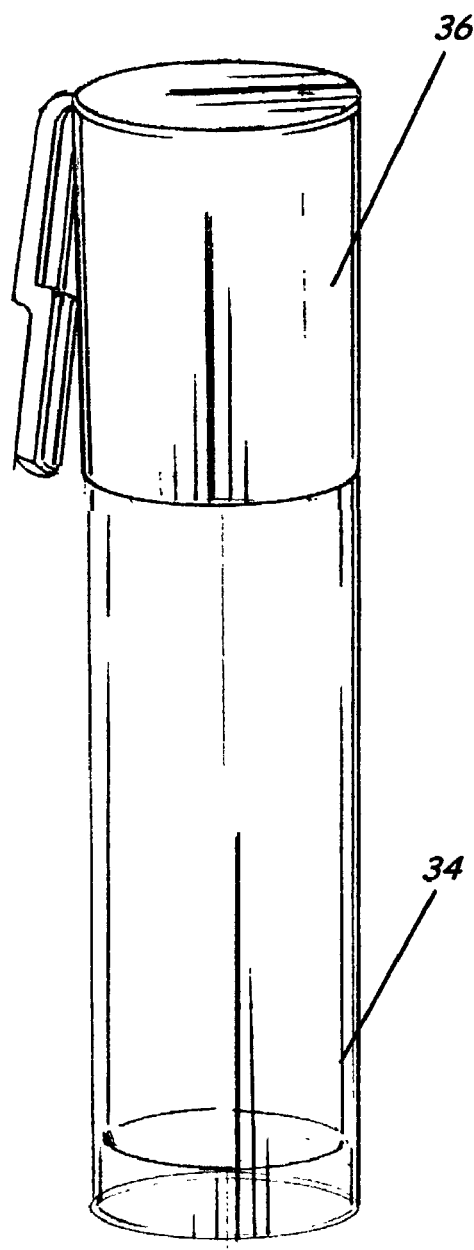
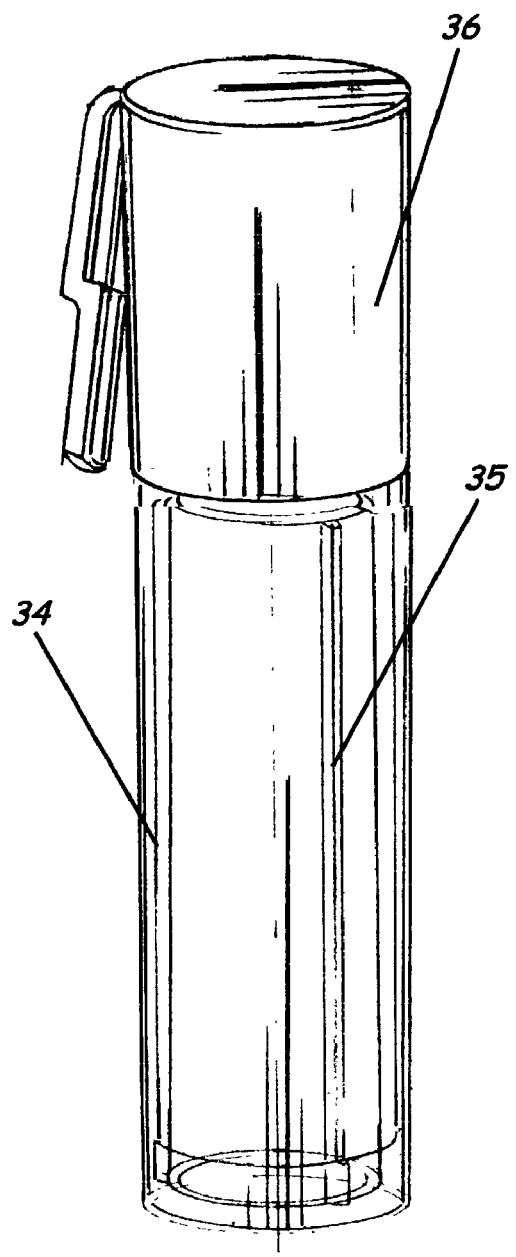

METHOD, SYSTEM AND KIT FOR TREATMENT OF PEYRONIE'S DISEASE

FIELD OF THE INVENTION

The present invention relates to the field of medical treatment and, more particularly, to a method, system and kit for treating plaque formation in a patient's extremity such as Peyronie's Disease in a male sexual organ.

BACKGROUND OF THE INVENTION

Peyronie's disease is a condition characterized by the development of fibrous nodules or lumps in the substance of the penis. It is estimated that it afflicts about 1% of the adult male population. A study of the cross section of the penis in the human male shows that the organ has many layers. Peyronie's disease affects the tunica albuginea layer of the penis. It is most common between ages 40 and 70 but no age is exempt. Even boys in their teens with Peyronie's disease have been described. The exact cause of this disease is not known and many theories abound about the probable mechanism of occurrence of the condition.

An association with abnormal scar tissue formation elsewhere in the body, such as the plantar fascia of the foot, known as Lederhose's disease; the eardrum, known as tympanosclerosis; and the palm of the hand, known as Dupuytren's contracture; is well-known. Approximately 10% of patients with Peyronie's disease also have a Dupuytren's contracture or "trigger finger".

Evaluation of Peyronie's disease addresses not only the penile curvature but also any associated erectile dysfunction, as both of these problems are often present at the same time. Erectile dysfunction may occur because the plaque may interfere with the ability of the muscles within the corpora to compress the veins that drain the penis during an erection. Therefore, blood "leaks" from the penis back into the general circulation, making it impossible to maintain an erection.

Men with Peyronie's disease usually seek medical attention because of painful erections and difficulty with intercourse. Since the cause of the disease and its development are not well understood, doctors treat the disease empirically; that is, they prescribe and continue methods that seem to help and have been used in the past. The goal of therapy is to keep the Peyronie's patient sexually active. Providing education about the disease and its course often is all that is required. No strong evidence shows that any treatment other than surgery is effective. Experts usually recommend surgery only in long-term cases in which the disease is stabilized and the deformity prevents intercourse.

Because the course of Peyronie's disease is different in each patient and some patients experience improvement without treatment, medical experts suggest waiting 1 to 2 years or longer before attempting to correct it surgically. During that wait, patients are often willing to undergo treatments whose effectiveness has not been proven.

Some researchers have given men with Peyronie's disease vitamin E orally in small-scale studies and have reported improvements. No controlled studies have established the effectiveness of vitamin E therapy, however. Similar inconclusive success has been attributed to oral application of para-aminobenzoate, a substance belonging to the family of B-complex molecules.

Researchers have injected chemical agents such as verapamil, collagenase, steroids, and calcium channel blockers directly into the plaques. These interventions are still considered unproven because studies have included low numbers of patients and have lacked adequate control groups.

Steroids, such as cortisone, have produced unwanted side effects, such as atrophy or death of healthy tissues. Another intervention involves iontophoresis, the use of a painless current of electricity to deliver verapamil or some other agent under the skin directly to the plaque.

Radiation therapy, in which high-energy rays are aimed at the plaque, has also been used. Like some of the chemical treatments, radiation appears to reduce pain, but it has no effect at all on the plaque itself and can cause unwelcome side effects. Although the variety of agents and methods used points to the lack of a proven treatment, new insights into the wound healing process may yield more effective therapies in the near future.

Peyronie's disease has been treated with some success by surgery. The two most common surgical methods are removal or expansion of the plaque. This is followed by placement of a patch of skin or artificial material, and removal or pinching of tissue from the side of the penis opposite the plaque, which cancels out the bending effect. The first method can involve partial loss of erectile function, especially rigidity. The second method, known as the Nesbit procedure, causes a shortening of the erect penis.

Some men choose to receive an implanted device that increases rigidity of the penis. In some cases, an implant alone will straighten the penis adequately. In other cases, implantation is combined with a technique of incisions and grafting or plication (pinching or folding the skin) if the implant alone does not straighten the penis.

Most types of surgery produce positive results. Because of complications and many of the phenomena associated with Peyronie's disease (for example, shortening of the penis), however, most doctors prefer to perform surgery only on the small number of men with curvature so severe that it prevents sexual intercourse.

Vacuum therapy only recently has been used to treat Peyronie's disease. Chris Spivey, a surgical physician assistant at Urology Centers of Alabama in Birmingham has been using the Spivey Technique™ for the treatment of Peyronie's disease over a period of time and through a process of adapting vacuum therapy through existing vacuum cylinders used to treat impotence. There is still a need to improve the vacuum therapy techniques for treating Peyronie's disease.

SUMMARY OF THE INVENTION

With the foregoing in mind, an embodiment of the present invention advantageously provides non-invasive and non-surgical methods for treating plaque formation in a patient's extremity such as Peyronie's disease. Also, an embodiment of the present invention advantageously provides a kit and a system for treating plaque formation in a patient's extremity non-invasively and non-surgically.

More specifically, an embodiment of the present invention advantageously provides a kit for treating plaque formation in a patient's extremity. This kit preferably includes a pressure pump and at least two elongated vacuum chambers positioned in a container. Each of the at least two vacuum chambers preferably has a proximal and distal longitudinal ends. The proximal end is preferably adapted to receive a patient's extremity, and a distal longitudinal end adapted to be positioned in fluid communication with the pressure pump. When the pressure pump is operating, a pressure is created inside each of the at least two vacuum chambers and exerted upon the extremity received therein.

Preferably, the at least two vacuum chambers have different inner circumferences. When the pressure pump is operating, a different level of prevention from bending is provided to the extremity in the direction of the plaque formation with each of the at least two vacuum chambers.

An embodiment of the present invention also advantageously provides a system for treating plaque formation in a patient's extremity. This system preferably includes a pressure pump and an elongated vacuum chamber. The vacuum chamber is positioned in fluid communication with the pressure pump at a distal longitudinal end thereof. At a proximal longitudinal end, the vacuum chamber is to receive a patient's extremity. The at least two vacuum chambers preferably have a different inner circumference than another one of the at least two vacuum chambers so that a different level of prevention from bending is provided to the extremity in the direction of the plaque formation with each of the at least two vacuum chambers during operation of the pressure pump.

Additionally, the present invention advantageously includes a method of treating plaque formation in a patient's extremity. This method, for example, preferably includes preferably includes positioning a first elongated vacuum chamber inside a second elongated vacuum chamber, placing a patient's extremity inside the first vacuum chamber from a proximal longitudinal open end thereof, and pumping air out of the first vacuum chamber from a distal longitudinal end thereof to create a pressure therewithin.

BRIEF DESCRIPTION OF THE DRAWING

Some of the features, advantages, and benefits of the present invention having been stated, others will become apparent as the description proceeds when taken in conjunction with the accompanying drawings in which:

FIG. 3A is a front elevational view of an inner vacuum chamber shown in FIG. 2 according to an embodiment of the present invention;

FIG. 3B is a sectional view taken along line 3B—3B of FIG. 3A according to an embodiment of the present invention;

FIG. 6 is a perspective view of a system used for treating plaque formation in a patient's extremity according to another embodiment of the present invention;

FIG. 7 is a perspective view of a system used for treating plaque formation in a patient's extremity according to another embodiment of the present invention;

FIG. 8 is a perspective view of a system used for treating plaque formation in a patient's extremity according to another embodiment of the present invention;

FIG. 9 is a perspective view of a system used for treating plaque formation in a patient's extremity according to another embodiment of the present invention;

DETAILED DESCRIPTION

The present invention will now be described more fully hereinafter with reference to the accompanying drawings which illustrate various embodiments of the invention. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime or double prime notation, if used, indicate similar elements in alternative embodiments.

As illustrated in FIGS. 1–4, a kit for treating plaque formation in an extremity of a patient is advantageously placed in a container. This kit preferably includes at least two elongated vacuum chambers and a pressure pump. Each of the at least two elongated vacuum chambers preferably has a proximal and distal longitudinal ends. The proximal end is referred to the end brought into contact with a user during operation while an opposite distal end is generally away from the body (i.e., torso) of the user. In this case, the end close to the patient's extremity is referred to as the proximal end. The proximal longitudinal end of each of the vacuum chambers is adapted to receive a patient's extremity and a distal longitudinal end adapted to be positioned in fluid communication with the pressure pump. When the pressure pump is operating, a pressure is created inside the chamber and exerted upon the extremity received therein.

Preferably, the at least two vacuum chambers have different inner circumferences. When the pressure pump is in operation, a different level of prevention from bending is provided to the extremity in the direction of the plaque formation with each of the at least two vacuum chambers.

Figure 1:
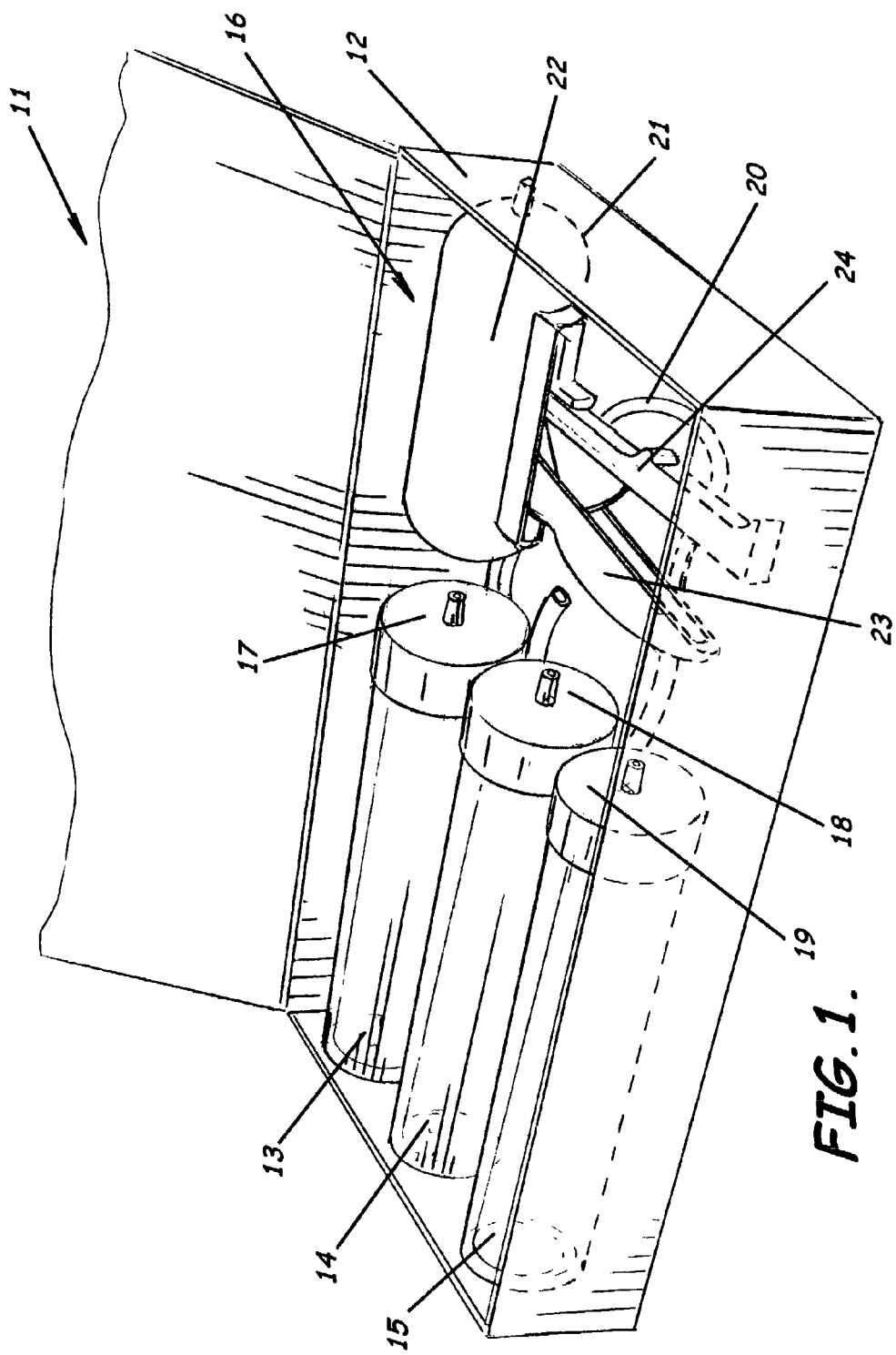
FIG. 1 is a perspective view of a kit for treating plaque formation in a patient's extremity according to an embodiment of the present invention.

As specifically illustrated in FIG. 1, for example, a kit 11 for treating plaque formation in an extremity of a patient preferably includes three elongated vacuum chambers 13, 14, 15 and a pressure pump 16 positioned in a container 12. Each of the three vacuum chambers 13, 14, 15 preferably has a different inner circumference than each of the other ones of the three vacuum chambers (referred to as small, medium and large chambers). When each of the three vacuum chambers 13, 14, 15 is used during operation of the pressure pump 16, a different level of prevention from bending is provided to the extremity in the direction of the plaque formation.

The kit 11 further preferably includes fluid communication establishing means 17, 18, 19 adapted to be connected to each of the three vacuum chambers 13, 14, 15, respectively, for establishing fluid communication between each of the three vacuum chambers 13, 14, 15 and the pressure pump 16. Further preferably included in the kit 11 is a flexible tube 20, which has a first end adapted to be connected to the fluid communication establishing means 17, 18, 19 separately and a second end adapted to be connected to the pressure pump 16.

As further illustrated in FIG. 1, the pressure pump 16 preferably includes a pump housing 21, a pump actuator 22 positioned in the pump 16, a handle 23 connected to the housing 21, and a pump actuation arm 24 connected to the housing 21 and to the pump actuator 22. When pulling the actuation arm 24 toward the handle 23, one actuates the pressure pump 16. Once the pressure pump 16 is actuated, air is drawn out of the vacuum chambers 13, 14, 15, causing negative pressure (i.e., vacuum) to be created inside the chambers. This negative pressure causes blood to be drawn into vascular system of a patient's extremity creating pressure to stretch the plaque formed in the extremity. The sides of the vacuum chambers prevent the extremity from bending in the direction of the plaque formation, which further stretches the scar tissue.

The pressure pump 16 further advantageously has a built-in pressure limiter. This limiter automatically restricts the amount of negative pressure that can be drawn to a pre-set safe limit. The limiter is located inside the pump and pre-set at the manufacture. The pressure pump handle 23 has a negative pressure release located just above the handle. Pressure is released when the handle 23 is pulled toward a user. The mount of pressure released is related to how much the handle is pulled. The more the handle is pulled, the more pressure is released. In the event of too much pressure being drawn during use, one may release gradual amounts of negative pressure until the desired level is achieved.

Figure 2:
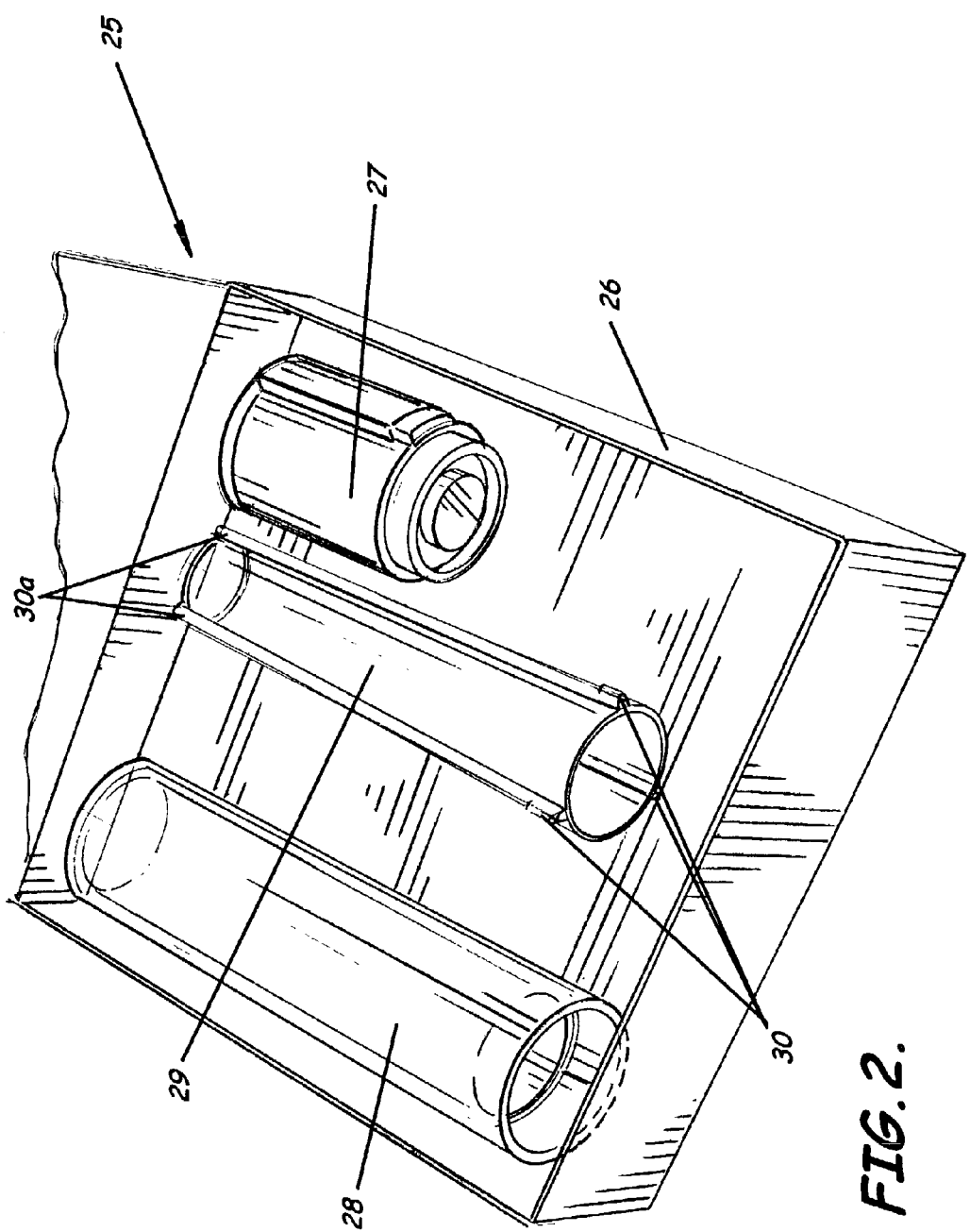
FIG. 2 is a perspective view of a kit for treating plaque formation in a patient's extremity according to another embodiment of the present invention.
Figures 3C, 3D:
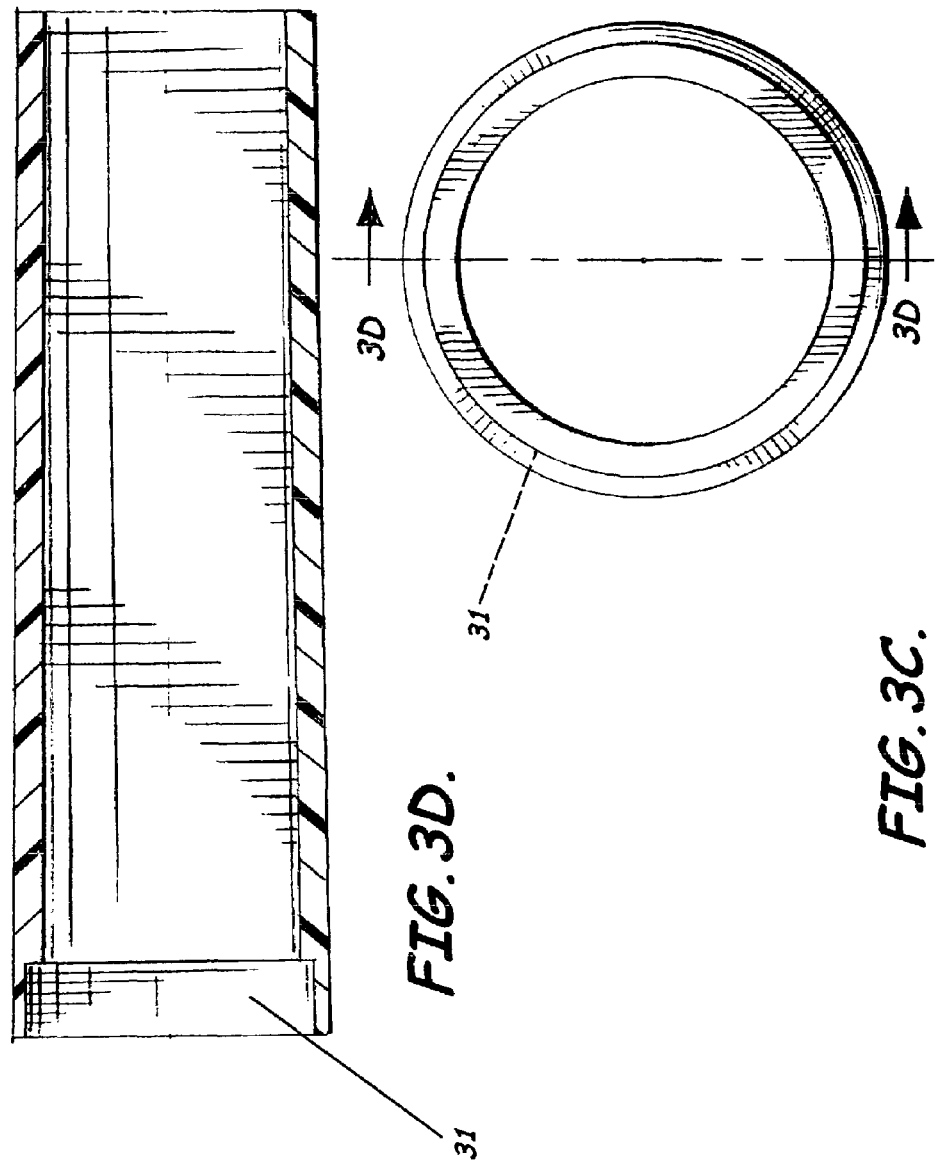
FIG. 3C is a front elevational view of an outer vacuum chamber shown in FIG. 2 according to an embodiment of the present invention.
FIG. 3D is a sectional view taken along line 3D—3D of FIG. 3C according to an embodiment of the present invention.

Illustrated in FIG. 2 is another example of a kit for treating plaque formation in an extremity of a patient. This kit 25, for example, preferably includes a pressure pump 27, an outer vacuum chamber 28 and at least one inner vacuum chamber 29 positioned in a container 26. The inner vacuum chamber 29 is adapted to be inserted into the outer vacuum chamber 28. Each of the outer vacuum chamber 28 and the inner vacuum chamber 29 preferably has a proximal longitudinal end adapted to receive a patient's extremity at a preselected time upon a predetermined condition of the patient's extremity and a distal longitudinal end adapted to be positioned in fluid communication with the pressure pump 27. Depending on the timing during a course of a treatment and condition of the extremity, the outer vacuum chamber 28 may be connected to and in fluid communication with the pressure pump 27 without the inner vacuum chamber 29 positioned therein. Since the outer vacuum chamber 28 preferably has a different inner circumference than the inner vacuum chamber 29, a different level of prevention from bending is provided to the patient's extremity in the direction of the plaque formation with each of the outer vacuum chamber 28 and the inner vacuum chamber 29 positioned within the outer vacuum chamber 28 during operation of the pressure pump 27.

FIGS. 3A, 3B, 4A and 4B illustrate interfacing means between the outer surface of the inner vacuum chamber 29 and the inner surface of the outer vacuum chamber 28 shown in FIG. 2. The outer vacuum chamber 28 preferably has an inner flange 31, which is positioned adjacent the proximal longitudinal end of the outer chamber 28 and connected to and extending inwardly from an inner surface of the outer chamber 28. Thereby, an inner step is defined and formed therein from the proximal longitudinal end of the outer chamber 28. In the other hand, the inner vacuum chamber 29 preferably has a plurality of stop members 30 extending outwardly from an outer surface of the inner vacuum chamber 29 to interface with and contact the inner step 31 of the outer vacuum chamber 28 to thereby limit the inward movement of the inner vacuum chamber 29 when positioned within the outer vacuum chamber 28. Further preferably, the inner vacuum chamber 29 has a plurality of spaced-apart ribs 30-*a* connected to and extending outwardly from the outer surface, which provides separation between the outer surface of the inner vacuum chamber 29 and the inner surface of the outer vacuum chamber 28. Therefore, an interstitial space is formed between the two surfaces when the inner vacuum chamber 29 is positioned within the outer vacuum chamber 28.

Figure 4:
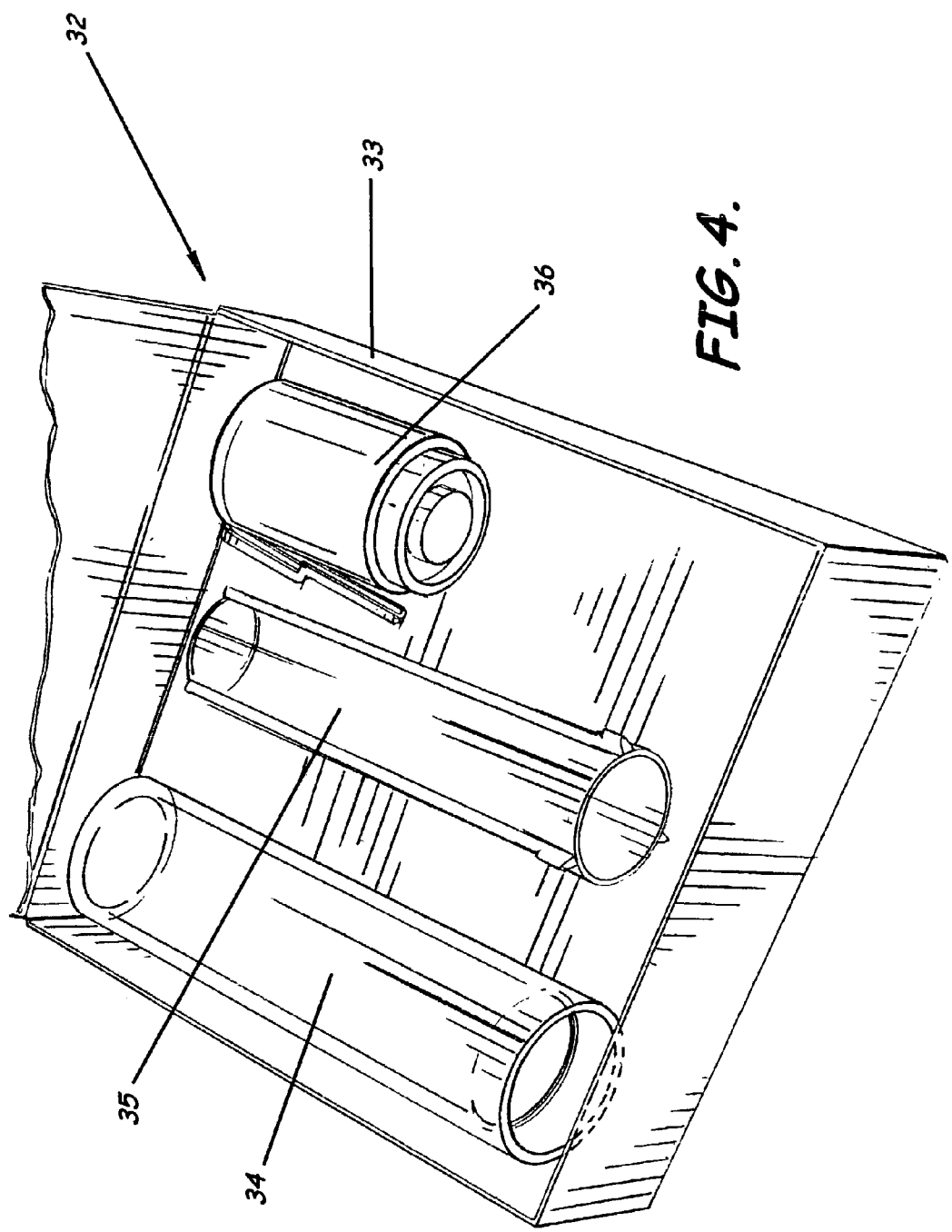
FIG. 4 is a perspective view of a kit for treating plaque formation in a patient's extremity according to another embodiment of the present invention.

Illustrated in FIG. 4 is another example of a kit for treating plaque formation in an extremity of a patient. The kit 32, for example, preferably includes a pressure pump 36, an outer vacuum chamber 34 and at least one inner vacuum chamber 35 positioned in a container 33. The inner vacuum chamber 35 is adapted to be inserted into the outer vacuum chamber 34. Each of the outer vacuum chamber 34 and the inner vacuum chamber 35 preferably has a proximal longitudinal end adapted to receive a patient's extremity at a preselected time upon a predetermined condition of the patient's extremity and a distal longitudinal end adapted to be positioned in fluid communication with the pressure pump 36. Depending on the timing during a course of a treatment and condition of the extremity, the outer vacuum chamber 34 may be connected to and in fluid communication with the pressure pump 36 without the inner vacuum chamber 35 positioned therein. Since the outer vacuum chamber 34 preferably has a different inner circumference than the inner vacuum chamber 35, a different level of prevention from bending is provided to the patient's extremity in the direction of the plaque formation with each of the outer vacuum chamber 34 and the inner vacuum chamber 35 positioned within the outer vacuum chamber 34 during operation of the pressure pump 36.

The difference between the kit 25 illustrated in FIG. 2 and kit 32 illustrated in FIG. 4 is that the pressure pump 27 in kit 25 is a battery-driven pump, whereas the pressure pump 36 in kit 32 is a manual pump. For the battery-driven pump 27, one operates the pump by simply touching a button. Soma Blue Touch®II vacuum system uses such a battery-driven pump. While for the manual pump 36, one operates the pump by pulling a handle attached to the pump body towards the pump using just one finger. Soma Blue Response®II provides such an example.

Further as illustrated in FIGS. 1–4, the vacuum chambers preferably have a substantially cylindrical shape. One example of the extremity is a male sexual organ, and the plaque formation preferably includes Peyronie's disease in the male sexual organ.

The present invention also advantageously provides a system for treating plaque formation in a patient's extremity. This system preferably includes a pressure pump and one of at least two elongated vacuum chambers. The one vacuum chamber is positioned in fluid communication with the pressure pump at a distal longitudinal end thereof and is adapted to receive a patient's extremity at a proximal longitudinal end thereof. The one vacuum chamber preferably has a different inner circumference than another one of the at least two vacuum chambers so that a different level of prevention from bending is provided to the extremity in the direction of the plaque formation with each of the at least two vacuum chambers during operation of the pressure pump.

Figure 5:
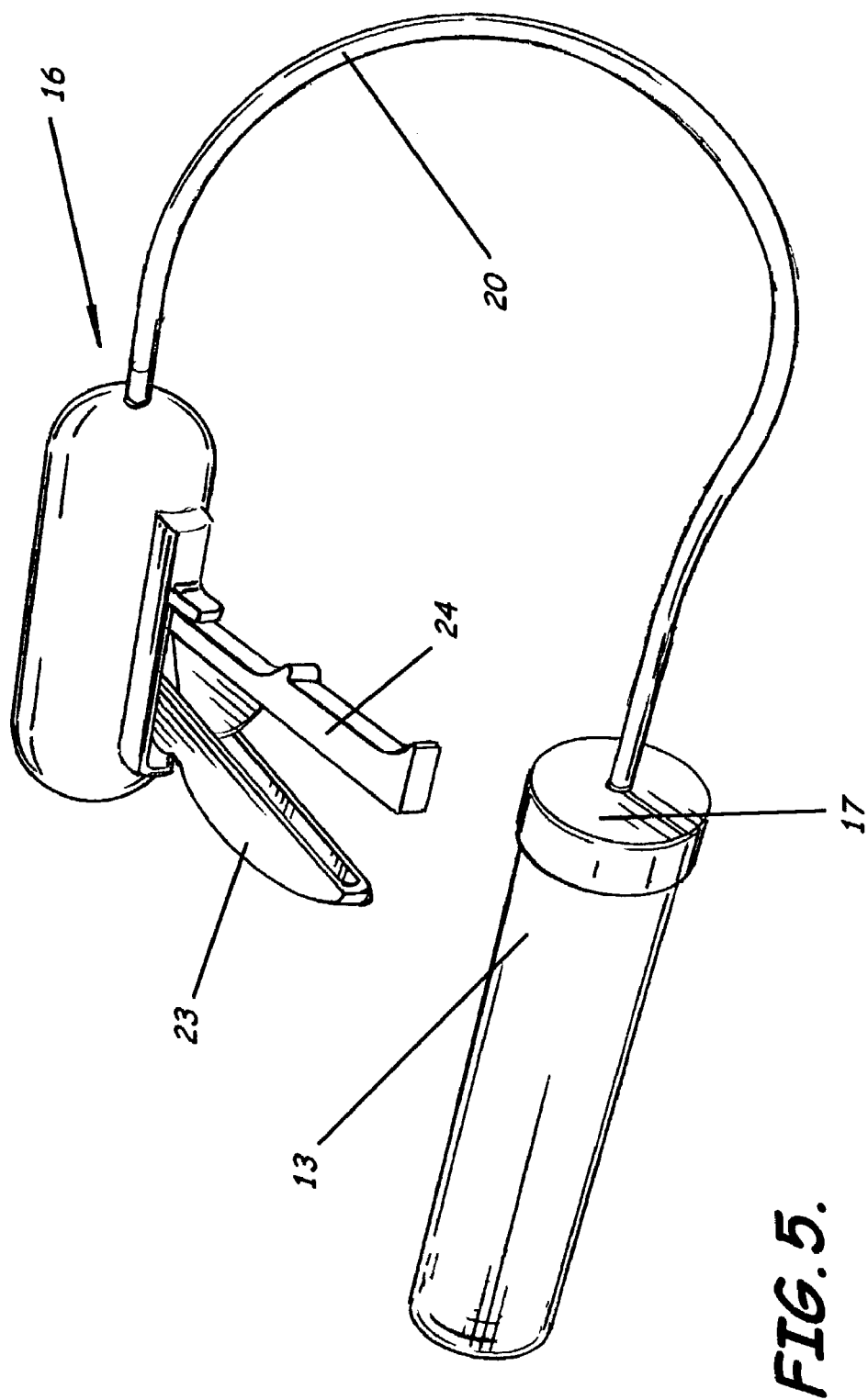
FIG. 5 is a perspective view of a system used for treating plaque formation in a patient's extremity according to an embodiment of the present invention.

As specifically illustrated in FIG. 5, for example, a system for treating plaque formation in an extremity preferably includes an elongated vacuum chamber 13, a pressure pump 16, fluid communication means 17 connected to the vacuum chamber 13 for establishing fluid communication between the chamber 13 and the pump 16, and a flexible tube 20 connected to the fluid communication means 17 and the pressure pump 16. One operates the pressure pump 16 by pulling the actuation arm 24 toward the handle 23.

In this system, the vacuum chamber 13 is adapted to receive a patient's extremity at a proximal longitudinal end of the chamber. Depending on the timing during a course of a treatment and condition of the extremity, vacuum chambers having different inner circumferences (e.g., chamber 14 or chamber 15 in FIG. 1) than the vacuum chamber 13 can be used in place of the chamber 13. Therefore, a different level of prevention from bending is provided to the extremity in the direction of the plaque formation with each of the vacuum chambers during operation of the pressure pump.

Illustrated in FIGS. 6 and 7 are another example of a system for treating plaque formation in an extremity. This system preferably includes an outer vacuum chamber 28 and at least one inner vacuum chamber 29 adapted to be inserted into the outer vacuum chamber 28. Each of the outer chamber 28 and the inner chamber 29 preferably has a proximal longitudinal end adapted to receive a patient's extremity at a preselected time upon a predetermined condition of the patient's extremity and a distal longitudinal end adapted to be positioned in fluid communication with a pressure pump 27.

Depending on the timing during a course of a treatment and condition of the extremity, the outer vacuum chamber 28 may be connected to and in fluid communication with the pressure pump 27 without the inner vacuum chamber 29 positioned therein as illustrated in FIG. 6. Since the outer vacuum chamber 28 preferably has a different inner circumference than the inner vacuum chamber 29, a different level of prevention from bending is provided to the patient's extremity in the direction of the plaque formation with each of the outer vacuum chamber 28 (FIG. 6) and the inner vacuum chamber 29 positioned within the outer vacuum chamber 28 (FIG. 7) during operation of the pressure pump 27.

Illustrated in FIGS. 8 and 9 are yet another example of a system for treating plaque formation in an extremity. This system preferably includes an outer vacuum chamber 34 and at least one inner vacuum chamber 35 adapted to be inserted into the outer vacuum chamber 34. Each of the outer chamber 34 and the inner chamber 35 preferably has a proximal longitudinal end adapted to receive a patient's extremity at a preselected time upon a predetermined condition of the patient's extremity and a distal longitudinal end adapted to be positioned in fluid communication with a pressure pump 36.

Depending on the timing during a course of a treatment and condition of the extremity, the outer vacuum chamber 34 may be connected to and in fluid communication with the pressure pump 36 without the inner vacuum chamber 35 positioned therein as illustrated in FIG. 8. Since the outer vacuum chamber 34 preferably has a different inner circumference than the inner vacuum chamber 35, a different level of prevention from bending is provided to the patient's extremity in the direction of the plaque formation with each of the outer vacuum chamber 34 (FIG. 8) and the inner vacuum chamber 35 positioned within the outer vacuum chamber 28 (FIG. 9) during operation of the pressure pump 36.

The difference between the system illustrated in FIGS. 6–7 and system illustrated in FIGS. 8–9 is that the pressure pump 27 is a battery-driven pump, whereas the pressure pump 36 is a manual pump. For the battery-driven pump 27, one operates the pump by simply touching a button. Soma Blue Touch®II vacuum system uses such a battery-driven pump. While for the manual pump 36, one operates the pump by pulling a handle attached to the pump body towards the pump using just one finger. Soma Blue Response®II provides such an example.

The present invention further advantageously provides methods of treating plaque formation in a patient's extremity. For example, such a method preferably includes placing a patient's extremity inside a first elongated vacuum chamber from a proximal longitudinal open end thereof, pumping air out of the first vacuum chamber from a distal longitudinal end thereof to create a pressure therewithin, adjusting amount of the pressure to a level that is adequate to pull the patient's extremity tight without causing discomfort to the patient, removing the first vacuum chamber, replacing the first vacuum chamber with a second vacuum chamber, repeating the above steps in relation to the first vacuum chamber, removing the second vacuum chamber, replacing the second vacuum chamber with a third vacuum chamber, repeating the above steps in relation to the first vacuum chamber. All the above steps are repeated for continuous treatment. Preferably, each of the first, second and third vacuum chamber has a different inner circumference than each of the other ones. During the treatment, the proximal longitudinal open end of each of the vacuum chamber used is pressed against the patient's body to ensure an airtight seal.

Figure 10:
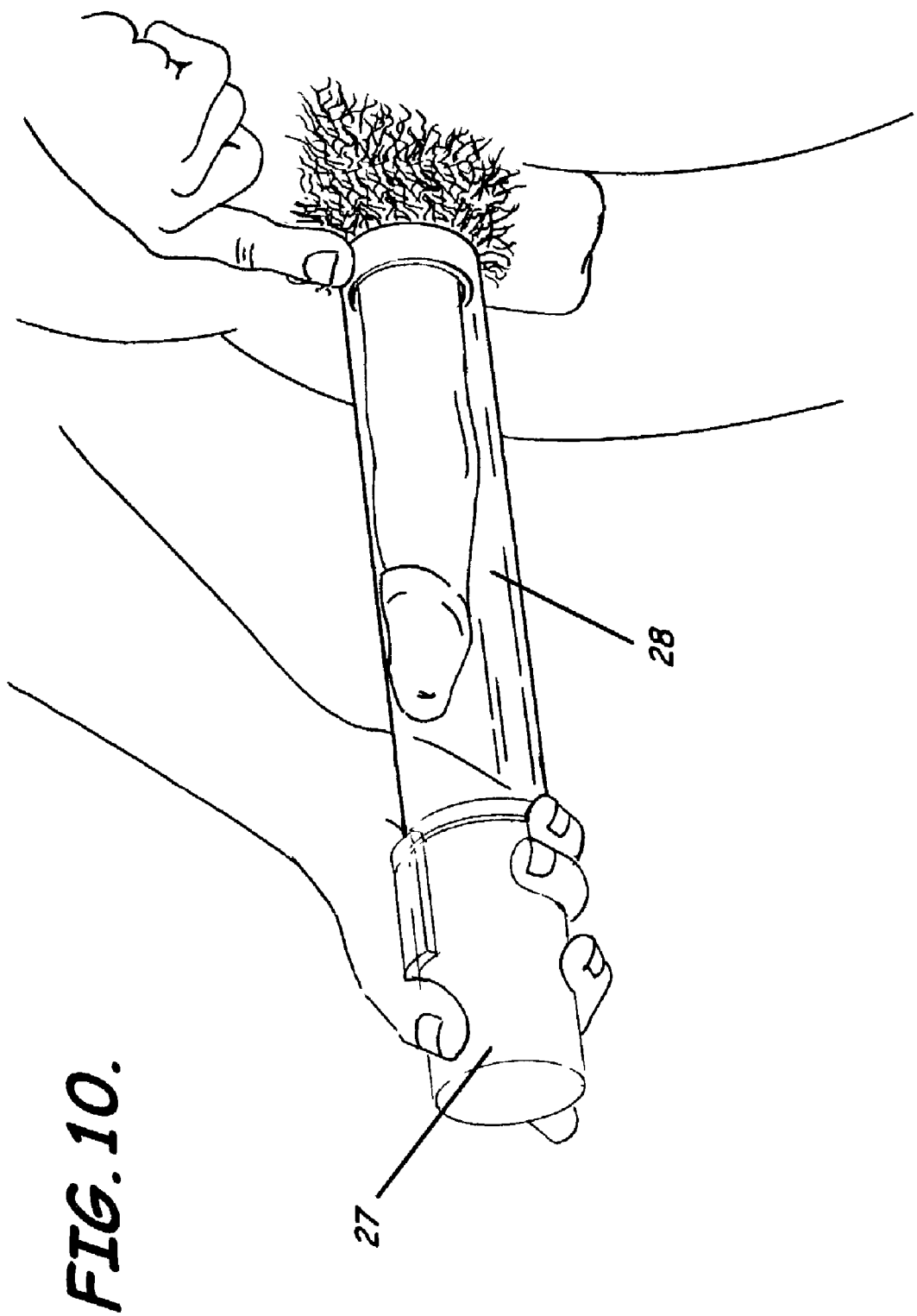
FIG. 10 is a schematic drawing showing the placement of a male sexual organ in a vacuum chamber during the treatment of Peyronie's disease according to an embodiment of the present invention.
Figure 11:
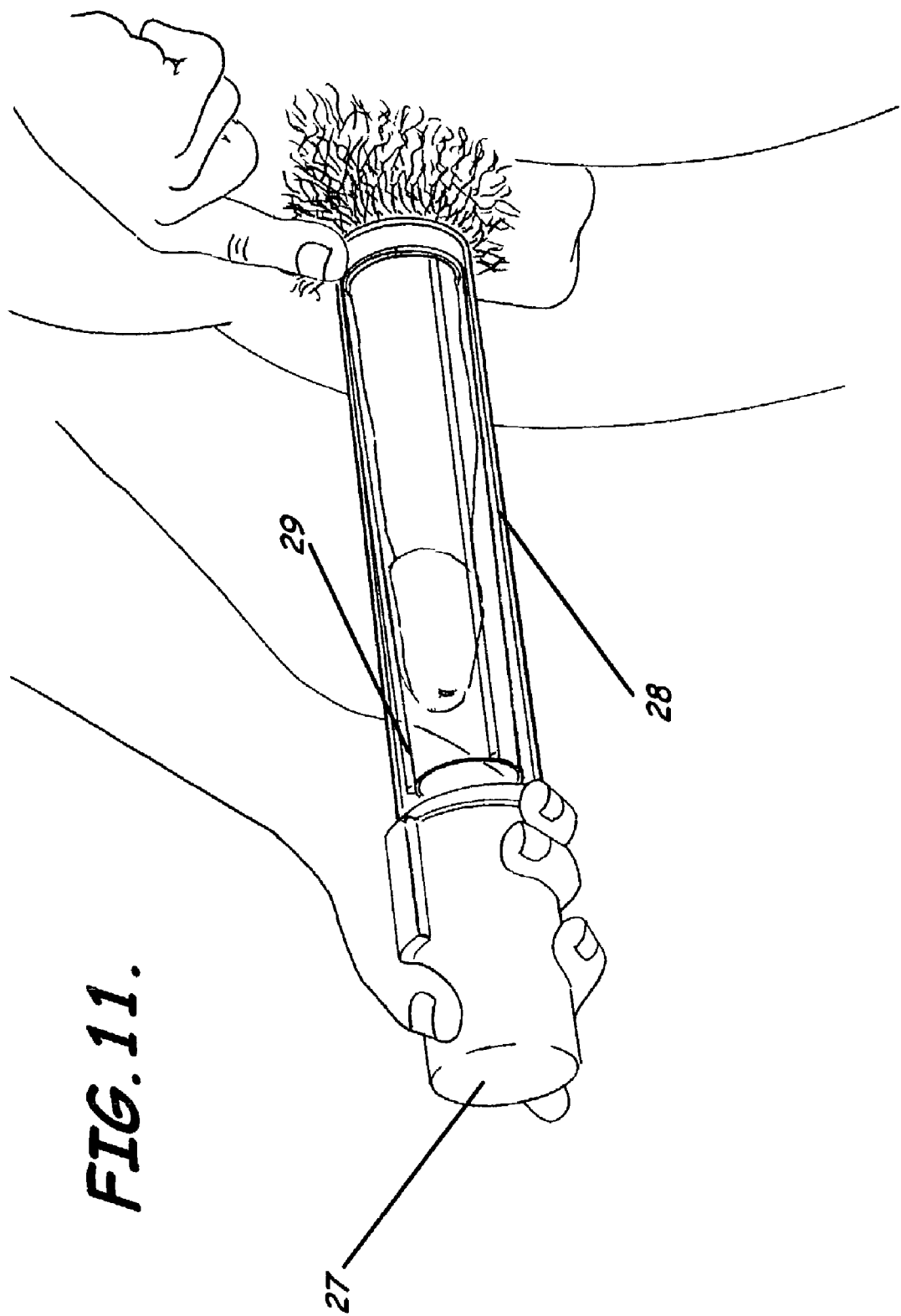
FIG. 11 is a schematic drawing showing the placement of a male sexual organ in a vacuum chamber during the treatment of Peyronie's disease according to another embodiment of the present invention.

As illustrated in FIGS. 10–11 is another method for treating plaque formation in a patient's extremity. This method, for example, preferably includes positioning a first elongated vacuum chamber 29 inside a second elongated vacuum chamber 28, placing a patient's extremity inside the first vacuum chamber 29 from a proximal longitudinal open end thereof, and pumping air out of the first vacuum chamber from a distal longitudinal end thereof to create a pressure therewithin. This method further preferably includes adjusting amount of the pressure to a level that is adequate to pull the patient's extremity tight without causing discomfort to the patient, removing the first vacuum chamber 29 from the second vacuum chamber 28, placing the patient's extremity inside the second vacuum chamber 28 from the proximal longitudinal open end thereof, and pumping air out of the second vacuum chamber 28 from the distal longitudinal end thereof to create a pressure therewithin. During the treatment, the proximal longitudinal open end of the inner or outer vacuum chamber is pressed against the patient's body to ensure an airtight seal.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

The invention claimed is:

1. A kit for treating plaque formation in a patient's extremity, the kit comprising:
   (a) a container;
   (b) a pressure pump positioned in the container; and (c) at least two noncontiguous elongated vacuum chambers positioned in the container and each having a proximal longitudinal end adapted to receive a patient's extremity and a distal longitudinal end adapted to be positioned in fluid communication with the pressure pump so that a pressure is created inside each of the at least two vacuum chambers and exerted upon the extremity received therein when the pressure pump is operating, one of the at least two vacuum chambers having a different inner circumference than another one of the at least two vacuum chambers so that a different level of prevention from bending is provided to the extremity in the direction of the plaque formation with each of the at least two vacuum chambers during operation of the pressure pump.

2. The kit of claim 1, wherein the at least two vacuum chambers comprises three vacuum chambers, each of the three vacuum chambers having a different inner circumference than each of the other ones of the three vacuum chambers so that a different level of prevention from bending is provided to the extremity in the direction of the plaque formation with each of the three vacuum chambers during operation of the pressure pump.

3. The kit of claim 2, wherein the kit further comprises fluid communication establishing means adapted to be connected to each of the three vacuum chambers for establishing fluid communication between each of the three vacuum chambers and the pressure pump, and at least one flexible tube having a first end adapted to be connected to the fluid communication establishing means and a second end adapted to be connected to the pressure pump.

4. The kit of claim 3, wherein the pressure pump comprises a pump housing, a pump actuator positioned in the pump, a handle connected to the housing, and a pump actuation arm connected to the housing and to the pump actuator so that movement of the actuation arm toward the handle by a user actuates the pressure pump.

5. The kit of claim 1, wherein the at least two vacuum chambers comprises an outer vacuum chamber and at least one inner vacuum chamber adapted to be inserted into the outer vacuum chamber, the outer vacuum chamber having a proximal longitudinal end adapted to receive a patient's extremity at a preselected time upon a predetermined condition of the patient's extremity and a distal longitudinal end adapted to be positioned in fluid communication with the pressure pump, the at least one inner vacuum chamber also having a proximal longitudinal end adapted to receive a patient's extremity at a preselected time upon a predetermined condition of the patient's extremity and a distal longitudinal end adapted to be positioned in fluid communication with the pressure pump, the outer vacuum chamber having a different inner circumference than the at least one inner vacuum chamber so that a different level of prevention from bending is provided to the patient's extremity in the direction of the plaque formation with each of the outer vacuum chamber and the at least one inner vacuum chamber during operation of the pressure pump.

6. The kit of claim 5, wherein the outer vacuum chamber includes interfacing means adapted to be positioned on an inner surface thereof for interfacing with the at least one inner vacuum chamber.

7. The kit of claim 6, wherein the outer vacuum chamber interfacing means comprises an inner flange positioned adjacent the proximal longitudinal end of the outer vacuum chamber and connected to and extending inwardly from an inner surface of the outer vacuum chamber to thereby define an inner step formed therein from the proximal longitudinal end thereof, and wherein the at least one inner vacuum chamber comprises a plurality of stop members extending outwardly from an outer surface of the at least one inner vacuum chamber to interface with and contact the inner step of the outer vacuum chamber to thereby limit the inward movement of the at least one inner vacuum chamber when positioned within the outer vacuum chamber.

8. The kit of claim 7, wherein the at least one inner vacuum chamber further comprises a plurality of spaced-apart ribs connected to and extending outwardly from the outer surface thereof to provide separation between the outer surface of the at least one inner vacuum chamber and the inner surface of the outer vacuum chamber so that an interstitial space is formed therebetween when the at least one inner vacuum chamber is positioned within the outer vacuum chamber.

9. The kit of claim 1, wherein the at least two vacuum chambers each has a substantially cylindrical shape, wherein the patient's extremity comprises a male sexual organ, and wherein the plaque formation comprises Peyronie's Disease in the male sexual organ.

10. A system for treating plaque formation in a patient's extremity, the system comprising:
  (a) a pressure pump; and
  (b) one of at least two elongated vacuum chambers positioned in fluid communication with the pressure pump at a distal longitudinal end thereof and adapted to receive a patient's extremity at a proximal longitudinal end thereof, one of the at least two vacuum chambers having a different inner circumference than another one of the at least two vacuum chambers so that a different level of prevention from bending is provided to the extremity in the direction of the plaque formation with each of the at least two vacuum chambers during operation of the pressure pump.

11. The system of claim 10, wherein the system comprises three vacuum chambers, each of the three chambers having a different inner circumference than each of the other ones of the three vacuum chambers so that a different level of prevention from bending is provided to the extremity in the direction of the plaque formation with each of the three vacuum chambers during operation of the pressure pump.

12. The system of claim 11, wherein the system further comprises:
  (a) fluid communication establishing means adapted to be connected to each of the three vacuum chambers for establishing fluid communication between each of the three vacuum chambers and the pressure pump; and
  (b) at least one flexible tube having a first end adapted to be connected to the fluid communication establishing means and a second end adapted to be connected to the pressure pump.

13. The system of claim 11, wherein the pressure pump comprises a pump housing, a pump actuator positioned in the pump, a handle connected to the housing, and a pump actuation arm connected to the housing and to the pump actuator so that movement of the actuation arm toward the handle by a user actuates the pressure pump.

14. The system of claim 10, wherein the system comprises an outer vacuum chamber and at least one inner vacuum chamber adapted to be inserted into the outer vacuum chamber, the outer vacuum chamber having a proximal longitudinal end adapted to receive a patient's extremity at a preselected time upon a predetermined condition of the patient's extremity and a distal longitudinal end adapted to be positioned in fluid communication with the pressure pump, the at least one inner vacuum chamber also having a proximal longitudinal end adapted to receive a patient's extremity at a preselected time upon a predetermined condition of the patient's extremity and a distal longitudinal end adapted to be positioned in fluid communication with the pressure pump, the outer vacuum chamber having a different inner circumference than the at least one inner vacuum chamber so that a different level of prevention from bending is provided to the patient's extremity in the direction of the plaque formation with each of the outer vacuum chamber and the at least one inner vacuum chamber during operation of the pressure pump.

15. The system of claim 14, wherein the outer vacuum chamber comprises interfacing means adapted to be positioned on an inner surface thereof for interfacing with the at least one inner vacuum chamber.

16. The system of claim 15, wherein the outer vacuum chamber interfacing means comprises an inner flange positioned adjacent the proximal longitudinal end of the outer vacuum chamber and connected to and extending inwardly from an inner surface of the outer vacuum chamber to thereby define an inner step formed therein from the proximal longitudinal end thereof, and wherein the at least one inner vacuum chamber comprises a plurality of stop members extending outwardly from an outer surface of the at least one inner vacuum chamber to interface with and contact the inner step of the outer vacuum chamber to thereby limit the inward movement of the at least one inner vacuum chamber when positioned within the outer vacuum chamber.

17. The system of claim 16, wherein the at least one inner vacuum chamber further comprises a plurality of spaced-apart ribs connected to and extending outwardly from the outer surface thereof to provide separation between the outer surface of the at least one inner vacuum chamber and the inner surface of the outer vacuum chamber so that an interstitial space is formed therebetween when the at least one inner vacuum chamber is positioned within the outer vacuum chamber.

18. The system of claim 10, wherein the at least two vacuum chambers each has a substantially cylindrical shape, wherein the patient's extremity comprises a male sexual organ, and wherein the plaque formation comprises Peyronie's Disease in the male sexual organ.

19. A method for treating plaque formation in a patient's extremity, the method comprising the steps of:
(a) placing a patient's extremity inside a first elongated vacuum chamber from a proximal longitudinal open end thereof, the proximal longitudinal open end being pressed against the patient's body to ensure an airtight seal;
(b) pumping air out of the first vacuum chamber from a distal longitudinal end thereof to create a pressure therewithin;
(c) adjusting amount of the pressure to a level that is adequate to pull the patient's extremity tight without causing discomfort to the patient;
(d) removing the first vacuum chamber;
(e) replacing the first vacuum chamber with a second vacuum chamber, the second chamber having a different inner circumference than the first vacuum chamber;
(f) repeating steps (a)–(d);
(g) removing the second vacuum chamber;
(h) replacing the second vacuum chamber with a third vacuum chamber, the third vacuum chamber having a different inner circumference than the first and second vacuum chambers;
(i) repeating steps (a)–(d); and
(j) repeating steps (a)–(i).

20. A method for treating plaque formation in a patient's extremity, the method comprising the steps of:
(a) positioning a first elongated vacuum chamber inside a second elongated vacuum chamber, each of the first and second vacuum chambers having a proximal longitudinal open end adapted to receive a patient's extremity and a distal longitudinal end adapted to be in fluid communication with a pressure pump;
(b) placing a patient's extremity inside the first vacuum chamber from the proximal longitudinal open end thereof; and
(c) pumping air out of the first vacuum chamber from the distal longitudinal end thereof to create a pressure therewithin.

21. The method of claim 20, further comprising the steps of:
adjusting amount of the pressure to a level that is adequate to pull the patient's extremity tight without causing discomfort to the patient;
removing the first vacuum chamber from the second vacuum chamber;
placing the patient's extremity inside the second vacuum chamber from the proximal longitudinal open end thereof, the proximal longitudinal open end of the second vacuum chamber being pressed against the patient's body to ensure an airtight seal; and pumping air out of the second vacuum chamber from the distal longitudinal end thereof to create a pressure therewithin.

22. A kit for treating plaque formation in a patient's extremity, the kit comprising:
(a) a container;
(b) a pressure pump positioned in the container; and
(c) at least two elongated vacuum chambers positioned in the container, the at least two vacuum chambers comprising an outer vacuum chamber and at least one inner vacuum chamber adapted to be inserted into the outer vacuum chamber, the outer vacuum chamber having a proximal longitudinal end adapted to receive a patient's extremity at a preselected time upon a predetermined condition of the patient's extremity and a distal longitudinal end adapted to be positioned in fluid communication with the pressure pump, the at least one inner vacuum chamber also having a proximal longitudinal end adapted to receive a patient's extremity at a preselected time upon a predetermined condition of the patient's extremity and a distal longitudinal end adapted to be positioned in fluid communication with the pressure pump, the outer vacuum chamber having a different inner circumference than the at least one inner vacuum chamber so that a different level of prevention from bending is provided to the patient's extremity in the direction of the plaque formation with each of the outer vacuum chamber and the at least one inner vacuum chamber during operation of the pressure pump.

23. A system for treating plaque formation in a patient's extremity, the system comprising:
(a) a pressure pump; and
(b) one of at least two elongated vacuum chambers, the vacuum chambers comprising an outer vacuum chamber and at least one inner vacuum chamber adapted to be inserted into the outer vacuum chamber, the outer vacuum chamber having a proximal longitudinal end adapted to receive a patient's extremity at a preselected time upon a predetermined condition of the patient's extremity and a distal longitudinal end adapted to be positioned in fluid communication with the pressure pump, the at least one inner vacuum chamber also having a proximal longitudinal end adapted to receive a patient's extremity at a preselected time upon a predetermined condition of the patient's extremity and a distal longitudinal end adapted to be positioned in fluid communication with the pressure pump, the outer vacuum chamber having a different inner circumference than the at least one inner vacuum chamber so that a different level of prevention from bending is provided to the patient's extremity in the direction of the plaque formation with each of the outer vacuum chamber and the at least one inner vacuum chamber during operation of the pressure pump.

24. A method for treating plaque formation in a patient's extremity, the method comprising the steps of:
   (a) placing a patient's extremity inside a first elongated vacuum chamber from a proximal longitudinal open end thereof, the proximal longitudinal open end being pressed against the patient's body to ensure an airtight seal;
   (b) pumping air out of the first vacuum chamber from a distal longitudinal end thereof to create a pressure therewithin;
   (c) adjusting amount of the pressure to a level that is adequate to pull the patient's extremity tight without causing discomfort to the patient;
   (d) removing the first vacuum chamber;
   (e) replacing the first vacuum chamber with a second elongated vacuum chamber, the second chamber having a different inner circumference than the first vacuum chamber;
   (f) placing the patient's extremity inside the second vacuum chamber from a proximal longitudinal open end thereof, the proximal longitudinal open end being pressed against the patient's body to ensure an airtight seal;
   (g) pumping air out of the second vacuum chamber from a distal longitudinal end thereof to create a pressure therewithin;
   (h) adjusting amount of the pressure to a level that is adequate to pull the patient's extremity tight without causing discomfort to the patient; and
   (i) removing the second vacuum chamber.

25. A system for treating plaque formation in a patient's extremity, the system comprising:
   (a) a pressure pump; and
   (b) one of at least two elongated vacuum chambers positioned in fluid communication with the pressure pump at a distal longitudinal end thereof and adapted to receive a patient's extremity at a proximal longitudinal end thereof, one of the at least two vacuum chambers having a different inner circumference for substantially its entire length than another one of the at least two vacuum chambers so that a different level of prevention from bending is provided to the extremity in the direction of the plaque formation with each of the at least two vacuum chambers during operation of the pressure pump.

26. The system of claim 10, wherein the different inner circumference of one of the at least two vacuum chambers extends substantially the entire length of the vacuum chamber.

* * * * *

UNITED STATES PATENT AND TRADEMARK OFFICE
CERTIFICATE OF CORRECTION

| | |
|---|---|
| PATENT NO. | : 7,037,256 B2 |
| APPLICATION NO. | : 10/271821 |
| DATED | : May 2, 2006 |
| INVENTOR(S) | : Julian Osbon et al. |

It is certified that error appears in the above-identified patent and that said Letters Patent is hereby corrected as shown below:

Title page, item [73] should read
--Assignee: Augusta Medical Systems, LLC
　　　　　　1027 Broad Street
　　　　　　Augusta, Georgia 30903--

Signed and Sealed this

Twelfth Day of December, 2006

JON W. DUDAS
*Director of the United States Patent and Trademark Office*